United States Patent [19]

Kaiser

[11] Patent Number: 5,599,933
[45] Date of Patent: Feb. 4, 1997

[54] SURFACTANT COMPOSITION AND METHOD OF MAKING THE SAME

[75] Inventor: Richard J. Kaiser, Bethlehem, Pa.

[73] Assignee: Binney & Smith Inc., Easton, Pa.

[21] Appl. No.: 404,362

[22] Filed: Mar. 15, 1995

Related U.S. Application Data

[60] Continuation of Ser. No. 110,877, Aug. 24, 1993, abandoned, which is a division of Ser. No. 839,330, Feb. 20, 1992, Pat. No. 5,262,535.

[51] Int. Cl.$^6$ .................. C07D 295/00; C07D 265/30; C07F 9/28
[52] U.S. Cl. .................. 544/402; 544/158; 544/159; 544/358; 544/398; 562/30; 562/61; 562/62; 562/75; 562/82
[58] Field of Search .................. 544/159, 402; 562/30, 61, 62, 75, 82

[56] References Cited

U.S. PATENT DOCUMENTS

| | | | |
|---|---|---|---|
| 2,081,876 | 5/1937 | Prahl | 260/150 |
| 2,245,643 | 6/1941 | Borglin | 260/512 |
| 2,555,371 | 6/1951 | Prutton | 260/512 |
| 2,854,477 | 9/1958 | Steinhauer | 260/512 |
| 2,992,999 | 7/1961 | Smith et al. | 252/161 |
| 3,055,901 | 9/1962 | Speranza et al. | 260/268 |
| 3,110,683 | 11/1963 | Steinhauer et al. | 252/389 |
| 3,247,245 | 4/1966 | Teot et al. | 260/512 |
| 3,252,856 | 5/1966 | Steinhauer et al. | 167/30 |
| 3,264,242 | 8/1966 | Teot | 260/29.6 |
| 3,412,022 | 11/1968 | Obetz et al. | 252/8.7 |
| 3,529,015 | 9/1970 | Steinhauer et al. | 260/512 |
| 3,645,906 | 2/1972 | Valenta et al. | 252/171 |
| 3,856,858 | 12/1974 | Dighe et al. | 260/556 AR |
| 3,870,768 | 3/1975 | Blackwood et al. | 260/857 G |
| 3,915,825 | 10/1975 | Dighe et al. | 204/159.23 |
| 3,959,366 | 5/1976 | Dighe et al. | 260/543 R |
| 4,049,711 | 9/1977 | Kray | 260/551 |
| 4,066,395 | 1/1978 | Soiron et al. | 8/169 |
| 4,215,162 | 7/1980 | Kunnen et al. | 427/435 |
| 4,433,078 | 2/1984 | Kersten et al. | 523/404 |
| 4,463,157 | 7/1984 | Kersten et al. | 528/68 |
| 4,490,281 | 12/1984 | James et al. | 252/384 |
| 4,826,535 | 5/1989 | Godly | 106/499 |
| 4,859,778 | 8/1989 | Graeber et al. | 548/158 |
| 4,877,538 | 10/1989 | Kirjanov et al. | 252/8.7 |
| 4,948,892 | 8/1990 | Tanabe et al. | 544/360 |
| 5,043,089 | 8/1991 | Nollet et al. | 252/95 |
| 5,262,535 | 11/1993 | Kaiser | 544/402 |
| 5,312,481 | 5/1994 | Greiner | 106/157 |

FOREIGN PATENT DOCUMENTS

| | | |
|---|---|---|
| 541900 | 7/1957 | Canada . |
| 400835 | 5/1990 | European Pat. Off. . |
| 60-163801 | 8/1985 | Japan . |
| 61-246104 | 1/1986 | Japan . |
| 62-264053 | 11/1987 | Japan . |
| 912340 | 11/1959 | United Kingdom . |
| 1043043 | 1/1964 | United Kingdom . |

*Primary Examiner*—Cecilia Tsang
*Attorney, Agent, or Firm*—Leydig, Voit & Mayer, Ltd.

[57] ABSTRACT

The reaction product of:

(a) a compound of the formula:

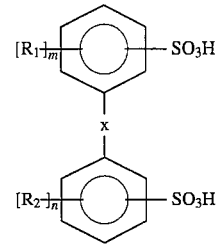

wherein X is a member selected from the group consisting of N, O and S; $R_1$ and $R_2$ are independently a straight or branched, saturated or unsaturated non-aromatic hydrocarbon of four to eighteen carbon atoms; m is 1 or 2; and n is 0, 1 or 2; and (b) a compound selected from the group consisting of primary, secondary, tertiary and higher amines, which are liquid at room temperature.

The reaction product of the present invention has excellent surfactant properties, and is suitable for use in coloring compositions to improve the fugitivity from skin and clothing. The reaction product is also useful as a cleansing agent.

15 Claims, No Drawings

SURFACTANT COMPOSITION AND METHOD OF MAKING THE SAME

This is a continuation of application Ser. No. 08/110,877, filed on Aug. 24, 1993 now abandoned which was a division of Ser. No. 07/839,330 filed Feb. 20, 1992 now U.S. Pat. No. 5,262,535.

FIELD OF THE INVENTION

This invention relates in general to the field of surfactant compositions.

BACKGROUND OF THE INVENTION

Traditional inks and paints generally available for use by both adults and children exhibit several drawbacks in daily use. Spills of such coloring compositions lead to stained skin and clothing. Clothing is often mined by such stains as they fail to wash out even after several washings. Skin must often be washed several times to remove such stains.

Further, many such coloring compositions are deficient in that they bleed through paper, commonly known as "strike-through". Addition of traditional surfactants to these compositions in attempts to improve fugitivity of the coloring compositions from skin and clothing merely increases strike-through.

Currently, some approaches to developing coloring compositions which are more easily washed from skin and textiles include (1) utilizing limitedly available dyes which have good fugitivity from fabrics and/or lowering dye concentrations and, (2) chemically grafting chromophores (dyes) onto a water soluble polymer such as poly(ethylene glycol). A major drawback to these methods is that they are costly.

Surfactants are commonly used to enhance the fugitivity and cleansing properties of compositions by altering the surface energy of a solid or liquid. This ability is attributable to the dual nature of the molecules or ions of the surfactant compositions. Within a single molecule or ion of a surface-active agent, there is a group that has a tendency to repel the dispersing medium or solvent, and at a suitable distance within the same molecule or ion, there is another group that attracts the dispersing medium or solution.

Typically, sulfonated surfactants are the most useful surface-active agents because they exhibit the most desirable fugitivity and cleansing properties. However, utilizing these sulfonated compounds is difficult because of the tendency of these compounds to remain in the solid state at room temperature.

In coloring compositions, such as those used in marking instruments, the tendency of a sulfonated surfactant to remain in the solid state at room temperature translates to clogging of the capillary marking system, such as a bonded fiber marker nib. Therefore, the caps on these capillary marking systems may only be removed for very short time periods before the marking system becomes inoperable.

Therefore, an object of the present invention is to provide a composition which imparts enhanced fugitivity when added to various coloring compositions.

A further object of the present invention is to provide a surfactant composition which reduces the likelihood of skin irritation should the composition contact the skin.

An additional object of the present invention is to provide a surfactant composition which remains in a liquid state at room temperature.

Still a further object of this invention is to provide a surfactant composition which may be manufactured economically.

These and other objects will become apparent to those skilled in the art to which the invention pertains.

SUMMARY OF THE INVENTION

The present invention overcomes the drawbacks associated with prior surfactant compositions by providing a new surfactant composition which, when added to coloring compositions, significantly increases the coloring compositions' fugitivity from fabrics and skin while largely preventing strike-through in paper.

The present invention imparts the desirable cleaning characteristics of traditional sulfonated surfactants while avoiding the solidification disadvantages of those surfactants. The composition of the present invention therefore imparts improved and convenient cleaning properties.

In general, the present invention is the reaction product of:

(a) A compound of the formula:

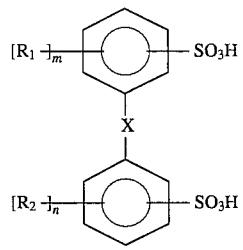

wherein X is a member selected from the group consisting of N, O and S; $R_1$ and $R_2$ are independently a straight or branched, saturated or unsaturated non-aromatic hydrocarbon of four to eighteen carbon atoms; m is 1 or 2; and n is 0, 1 or 2; and (b) a compound selected from the group consisting of primary, secondary, tertiary and higher amines, which are liquids at room temperature.

Primary amines are characterized by the $-CH_2NH_2$ group, while secondary amines contain the group $(-CH_2)_2NH$. Tertiary amines are tri-substituted amines characterized by the group $(-CH_2)_3N$, for example, trimethyl amine, $(CH_3)_3N$. Higher amines are amines which are a combination of primary, secondary or tertiary amines.

In one form, the present invention is a reaction product of: (a) a mono- or di- substituted diphenyl ether disulfonic acid ("DEDA") and (b) a member of the group consisting of primary, secondary, tertiary and higher amines. In one preferred form, the amine is N-aminoethylpiperazine ("N-AEP").

When the composition of the invention is a reaction product of a mono- or di- substituted DEDA and N-AEP, the reaction product would appear to be of the formula:

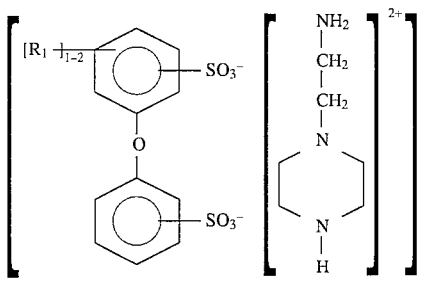

wherein $R_1$ is a branched or unbranched, saturated or unsaturated non-aromatic hydrocarbon of four to eighteen carbon atoms and wherein any two of the three nitrogen atoms in the amine moiety are protonated.

The composition of the present invention is useful as a surfactant. The composition is chemically compatible with a variety of acid and basic dyes as well as inks, paints and other marking compositions.

Further, the composition of the present invention is useful as a cleaning agent for such articles as plastics and vinyl.

DETAILED DESCRIPTION OF THE INVENTION

Reactions involving primary, secondary, tertiary and higher amines with various acids are well documented throughout the chemical literature. This invention involves reactions of substituted diphenyl ether disulfonic acids ("DEDA") with a member of the group consisting of primary, secondary, tertiary and higher amines.

Reacting these two reagents produces a resultant product with surfactant properties. Also, this product can be employed in amounts of about 10% to about 40% by weight in inks, paints and the like to increase fugitivity from fabrics and skin while largely preventing strike-through in paper.

In general, the present invention is the reaction product of:

(a) a compound of the formula:

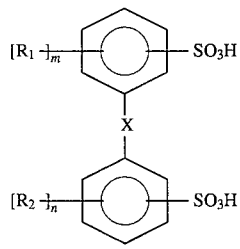

(I)

wherein X is a member selected from the group consisting of N, O and S; $R_1$ and $R_2$ are independently a straight or branched, saturated or unsaturated non-aromatic hydrocarbon of four to eighteen carbon atoms; m is 1 or 2; and n is 0, 1 or 2; and (b) a compound selected from the group consisting of primary, secondary, tertiary and higher amines, which are liquid at room temperature.

In one preferred form, the invention is a reaction product of: (a) a mono- or di- substituted diphenyl ether disulfonic acid ("DEDA") of the formula:

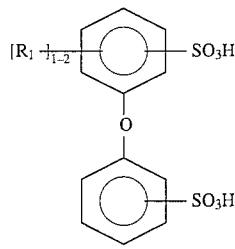

wherein $R_1$ is a straight or branched, saturated or unsaturated non-aromatic hydrocarbon of four to eighteen carbon atoms; and (b) a member of the group consisting of primary, secondary, tertiary and higher amines, which are liquid at room temperature.

Amines are organic compounds derived from ammonia by replacing one or more of the hydrogen atoms with organic radicals. Primary amines are characterized by the —$CH_2NH_2$ group, while secondary amines contain the group (—$CH_2)_2NH$. Tertiary amines are tri-substituted amines characterized by the group (—$CH_2)_3N$, for example, trimethyl amine, $(CH_3)_3N$. Higher amines are amines which are a combination of primary, secondary or tertiary amines.

Unexpectedly, N-aminoethylpiperazine ("N-AEP"), a higher amine which contains a primary, a secondary and a tertiary amine, is particularly appropriate for use. As a large molecule with a high molecular weight, N-AEP exhibits low mobility in solution, an attribute which is passed on to the reaction product of the invention. Low mobility is important in that it translates to less strike-through.

In addition to N-AEP, other suitable amines include primary amines such as N-butylamine; secondary amines such as ethylamino ethanol, butyl monoethanolamine, and diethylamine; tertiary amines such as diethylamino ethanol, ethyldiethanol amine, triethylamine, n-butyl diethanolamine, N-methyl morpholine, N-ethyl morpholine, and triethylene diamine; and higher amines such as dimethylaminopropylamine, which contains both a primary and a tertiary amine.

Like N-AEP, the above-mentioned compounds have high molecular weights, have boiling points greater than room temperature and are sufficiently basic to form the appropriate reaction products.

A preferred embodiment of the invention is the reaction product of dodecyl substituted DEDA and a member of the group consisting of primary, secondary, tertiary and higher amines, which are liquid at room temperature.

An even more preferred embodiment of the invention is the reaction product of mono- or di-dodecyl DEDA with N-AEP, the resulting reaction product appearing to be:

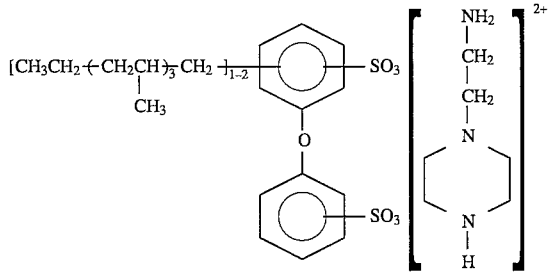

wherein any two of the three nitrogen atoms in the amine moiety are protonated to form ammonium ions. In other words, the hydrogen atoms can readily migrate from one site to another in the amine moiety.

Dodecyl DEDA is commercially available as an acid sold under the trademark "Poly-Tergent 2EP Acid" from Olin Chemical. This commercial preparation contains approximately 45% by weight of dodecyl DEDA and approximately 55% by weight of water. The reagent N-AEP is commercially available as a 100% liquid under the trademark "5379 N-Aminoethylpiperazine" sold by Texaco Chemical Company.

In general, the procedure for producing the reaction product of the present invention is the combination, usually by titration, of (a) a compound of formula I; and (b) a member of the group consisting of primary, secondary, tertiary and higher amines which are liquid at room temperature until a pH of about 7 to about 10, preferably from about 7 to about 8, and more preferably about 7.0, is achieved.

Specifically, the reaction of dodecyl DEDA with N-AEP is preferably carried out by adding from about 5% to about 15% by weight, preferably about 10% by weight of N-AEP, to from about 95% to about 85% by weight, preferably about 90% by weight of a commercial preparation containing approximately 45% by weight of dodecyl DEDA and approximately 55% by weight of water, and allowing the reaction to continue until a pH of about 7.0 to about 10.0, preferably until a pH of about 7.0 to 8.0, and most preferably until a pH of about 7.0 is achieved. This pH equates to from about 10% to about 30% N-AEP by weight, preferably 20% by weight N-AEP to from about 90% to about 70% by weight, preferably about 80% by weight of active dodecyl DEDA. The pH of the reaction may be checked by any conventional method. A suitable method for determining the pH is a pH meter. Heat is evolved in the neutralization reaction to the extent that the reactant temperature increases from 25° C. to about 50° C.

Typically, DEDA contains an excess of 2–3% sulfuric acid, which leads to the formation of piperazine sulfate when the N-AEP is added. The piperazine sulfate will eventually precipitate out of solution. Although piperazine sulfate is inert, the precipitate particle size is capable of plugging a capillary marking system such as a bonded fiber marker nib should the reaction product of the invention be used in a marking composition of such a system. Therefore, the piperazine sulfate precipitate should be removed from the reaction product. A suitable method for removing the precipitate is to filter the composition, as through a 30μ filter.

The resultant reaction product composition of the invention is useful in many applications. The composition improves skin and fabric fugitivity when used in coloring compositions such as dyes, inks and paints, and may also function as a cleansing agent.

The instant invention will be better understood by referring to the following examples.

Test Data and Examples

The composition of the present invention is chemically compatible with a variety of acid and basic dyes and inks formed using those coloring agents. Coloring compositions, such as an ink utilizing the present invention comprise from about 10% to about 40% by weight, preferably from about 20% to about 30% by weight, of the reaction product of the present invention; from about 40% to about 60% by weight, preferably about 43%, by weight, of deionized water ("DI"); and from about 0.5% to about 10.0% by weight, preferably about 4.0%, by weight, of a colorant.

The colorant may be an acid or basic dye. Typical dyes employed in the marking compositions of the present invention include acid red 1, acid red 388, acid yellow 23, acid-yellow 17, acid blue 9 and acid violet 12.

Optionally, the coloring composition may further comprise a humectant and preservatives such as biocides and fungicides.

Addition of humectant ensures that coloring compositions when in the form of an ink do not prematurely dry while in a capillary marking system, such as a bonded fiber marking nib. Typical humectants which may be employed in the coloring compositions of the present invention include polyhydric alcohols such as ethylene glycol, propylene glycol, hexylene glycol and poly(ethylene glycol), and hydroxylated starches. The humectant is preferably glycerin. The humectant is generally present from about 0% to about 30%, preferably about 22% by weight of the coloring composition.

Addition of preservatives inhibits the growth of bacteria and fungi in water-based products. A preferred biocide, "Nuosept 95", is a bicyclic oxazolidines solution and is commercially available from Hüls America, Inc. Nuosept 95 is a preferred biocide due to its chemical stability in coloring compositions. The biocide is generally present from about 0% to about 0.5%, preferably from about 0.06% to about 0.5%, and most preferably about 0.5% by weight of the composition. A preferred fungicide is "Polyphase P100" which is commercially available from Troy Chemical. Polyphase P100, principally containing 3-iodo 2-propynyl butyl carbamate, and generally represented by the formula, $C_8H_{12}INO_2$. Polyphase P100 is a preferred fungicide because it displays an exceptionally low order of toxicity. The fungicide is typically present from about 0% to about 2.5%, preferably about 0.08% to about 0.6%, and most preferably about 0.6% by weight of the composition.

Washable coloring compositions utilizing the present invention are preferably produced by blending together the deionized water, the humectant and other optional ingredients, if used, the reaction product of the present invention and the colorant.

Examples of washable coloring compositions utilizing the composition of the invention are as follows. Quantities are in percent by weight.

| WASHABLE COLORING COMPOSITIONS | | |
|---|---|---|
| Component | BLUE | GREEN |
| Deionized Water | 47.88 | 50.90 |
| Glycerin | 16.00 | 19.80 |
| Composition of Invention* | 32.00 | 25.20 |
| Acid Red 388 | 2.08 | — |
| Acid Yellow 17 | — | 3.00 |
| Acid Blue 9 | 1.54 | 0.60 |
| Nuosept 95 | 0.50 | 0.50 |

*Reaction product of dodecyl DEDA and N-AEP

Generally, from about 10% to about 40% by weight, and preferably from about 20% to about 30% by weight of the reaction product of the invention in an coloring composition provides an improved fugitivity from the skin, fabric or surfaces, by presumably blocking colorants from binding thereon. The fugitivity from skin of the coloring compositions combined with the reaction product of mono-dodecyl DEDA and N-AEP was measured by the following test:

1. Wash hands with soap and warm water. This pre-stain cleaning removes excess oil and dirt from the skin and provides a more consistent skin surface for testing. Allow the skin to dry for 30 seconds.

2. In the case of a marker containing the coloring composition, draw a stripe on the palm of the hand with the flat side of the nib. In the usual case, a ¼ inch wide by 1 inch long stripe works well. Apply enough pressure and/or multiple passes to make a comparison among two or more compositions. More than one stripe may be drawn. Let the stripes dry for 15 minutes.

3. Briefly rinse off the excess coloring composition from the marked hand with warm water.

4. Wash hands using a minimum amount of soap, rubbing hands together briskly with modest pressure for 30 seconds, then rinse away the soap.

5. Wipe hands dry with paper towels, and complete the drying with a relatively dry towel. A dry towel will help remove any residual traces of colorant.

6. Evaluate the removability of the coloring composition from skin by assigning a score using the following visual rating system:

5=no stain
4=barely visible
3=slight
2=moderate
1=severe

If removal of the marks was incomplete, repeat steps 4 through 6.

Skin wash testing was performed with coloring compositions comprising about 4.0% by weight of colorant; about 43% by weight of deionized water; about 22% by weight of glycerin; 0.5% by weight of biocide; 2.5% by weight of fungicide; and 28% by weight of the reaction product formed as a result of the reaction of the below listed amines with monododecyl substituted DEDA. The results were as follows:

| Compound | Skin Wash Rating |
| --- | --- |
| N-methyl morpholine | 3.0 |
| N-ethyl morpholine | 2.5 |
| N-AEP | 4.5 |
| ethylamino ethanol | 4.5 |
| ethyldiethanol amine | 4.5 |
| diethylamino ethanol | 4.0 |
| butyl monoethanolamine | 3.0 |
| n-butyl diethanolamine | 3.0 |
| diethylamine | 3.5 |
| triethylamine | 4.5 |
| N-butylamine | 4.0 |
| dimethylaninopropylamine | 3.5 |
| triethylene diamine | 3.5 |

The fugitivity from fabric of a coloring composition containing the composition of the present invention was tested by a standard wash test conducted on both 100 percent cotton fabric ("Fabric 419") and 50 percent cotton/50 percent polyester fabric ("Fabric 9406 WRL"). Children's clothing is constructed primarily from Fabric 9406 WRL. In the test, a washability value or "Delta E" was given to each surfactant tested. The higher the value of Delta E, the worse the stain remaining on the fabric. Generally, stains at 3.0 or under are considered acceptable by consumer standards.

The composition of the invention was tested in comparison to several commercially available cleaning agents. The cleaning agents included sodium dioctyl sulfosuccinate which is commercially available under the trademark "AEROSOL TO 75%" by American Cyanamid Company; sodium lauryl sulfate which is commercially available under the trademark "POLYSTEP-B5" by Stepan Co.; and propylene benzene sulfonic acid which is commercially available under the trademark "WITCO 1298HA" by Witco Organic Division.

About 28% by weight of each of the cleaning agents to be tested in the standard wash test were added to the coloring composition comprising about 43% of deionized water; about 4% of Acid Blue dye; about 28% by weight of glycerin; about 0.5% of a biocide; and about 2.5% by weight of fungicide.

| Cleaning Additive | Fabric 9406 WRL Delta E | Fabric 419 Delta E |
| --- | --- | --- |
| Composition of Invention* | 0.40 | 0.24 |
| Sodium dioctyl sulfosuccinate | 1.83 | 1.07 |
| Sodium lauryl sulfate | 2.09 | 0.56 |
| Propylene benzene sulfonic acid | 3.79 | 4.75 |

*Reaction product of dodecyl DEDA and N-AEP

The reaction product of the subject invention in coloring compositions containing dyes also permits a decrease in dye loading in the wash water during washing of fabric by holding and suspending the coloring composition on top of the wash water. Thus, the reaction product in the resultant coloring composition enhances the detergency of the composition as it is easily washable from fabrics.

In addition, coloring compositions containing from about 10% to about 40% by weight of the surfactant of the present invention have not been observed to cause skin irritation upon contact with the skin.

Generally, from about 10% to about 40%, preferably from about 20% to about 30% by weight of the reaction product of the subject invention in coloring compositions also improves the lightfastness and increases the brightness of said coloring compositions.

Addition of from about 10% to about 40%, preferably from about 20% to about 30%, by weight, of the reaction product of the invention to coloring compositions also inhibits the migration of the compositions through paper and other materials. As a result, strike-through of inks and paints containing the composition of the invention is decreased. These characteristics are believed to be attributable to the reaction product having large molecules with a high molecular weight. These large molecules have a low mobility. When added to coloring composition formulations, the resultant formulations have a low surface tension, a lower viscosity and a low mobility through paper, as well as on skin or other surfaces.

Adding an effective amount of the composition of the invention to coloring compositions does not alter the color of the composition. The color is not altered because the reaction product is chemically compatible with almost all conventional water-based coloring compositions.

When the reaction product is used in coloring compositions on paper, the colors are more uniform when dried than compositions without the reaction product. The reaction product allows the water borne composition to evenly wet papers fibers and results in the paper fibers being obscured. In systems without the reaction product, the dyes tend to settle in the depressions on either side of the fiber, thus highlighting the fiber.

Addition of from about 10% to about 40% by weight, preferably from about 20% to about 30% by weight of the reaction product of the invention to a paint composition comprising a water-based paint composition, effectively increases the fugitivity of the paint composition from fabric and skin. A preferred water-based liquid paint composition is tempera paint. Tempera paint is typically applied with a paint brush or similar instrument.

When the composition of the present invention is used in an ink composition, the solvent system may be an aqueous or non-aqueous system. Conventional non-aqueous solvents such as toluene, ketones, and oxygenated solvents are suitable.

The reaction product of the present invention also possesses desirable cleansing characteristics, and may be used as a cleansing agent for such products as vinyl and plastics. When used as a cleansing agent the reaction product of the invention is most suitably combined with a carrier. A preferred carrier is water. The reaction product is generally present in an amount from about 1.0% to about 50% by weight of the cleaning composition.

Those skilled in the art will understand that said invention is not limited by these examples which are offered merely as illustrations. Also those skilled in the art will understand that modifications can be made without departing from the spirit and scope of the invention.

What is claimed is:

1. A method of formulating a surfactant composition comprising reacting a sulfonic acid compound of the formula

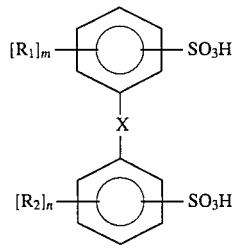

wherein X is a member selected from the group consisting of N, O and S; $R_1$ and $R_2$ are independently a straight or branched, saturated or unsaturated, nonaromatic hydrocarbon of four to eighteen carbon atoms, m is 1 or 2, and n is 0, 1, or 2; with an amine which is liquid at room temperature by:

(a) adding said amine and said sulfonic acid compound until a pH of from about 7.0 to about 10.0 is achieved.

2. The method according to claim 1, wherein said sulfonic acid compound is mono- or di- dodecyl diphenylether sulfonic acid.

3. The method according to claim 1, wherein said amine is selected from the group consisting of N-methylaminopiperazine, n-butylamine, ethylamino ethanol, butyl monoethanolamine, diethylamine, diethylaminoethanol, ethyl diethanolamine, n-butyl diethanolamine, N-methyl morpholine, N-ethyl morpholine, triethylene diamine, dimethylaminopropylamine, and combinations thereof.

4. The method according to claim 1, wherein said sulfonic acid compound is mono- or di- dodecyl diphenylether sulfonic acid and said amine is N-methylaminopiperazine.

5. The method according to claim 1, wherein said sulfonic acid compound and said amine are reacted by adding from about 10% to about 30% by weight of said amine and from about 90% to about 70% by weight of said sulfonic acid compound until a pH of from about 7.0 to about 10.0 is achieved.

6. The method according to claim 4, wherein said method of formulating further comprises removing any precipitate formed.

7. The method according to claim 6, wherein said precipitate is removed by filtration.

8. The method according to claim 7, wherein said filtration is conducted through a 30 micron filter.

9. A method of formulating a surfactant composition comprising reacting mono- or di- dodecyl diphenylether sulfonic acid and an amine which is liquid at room temperature.

10. The method according to claim 9, wherein said amine is selected from the group consisting of N-methylaminopiperazine, n-butylamine, ethylamino ethanol, butyl monoethanolamine, diethylamine, diethylaminoethanol, ethyl diethanolamine, n-butyl diethanolamine, N-methyl morpholine, N-ethyl morpholine, triethylene diamine, dimethylaminopropylamine, and combinations thereof.

11. The method according to claim 10, wherein said amine is N-methylaminopiperazine.

12. The method according to claim 11, wherein said sulfonic acid compound and said amine are reacted by adding from about 10% to about 30% by weight of said amine and from about 90% to about 70% by weight of said sulfonic acid until a pH of from about 7.0 to about 10.0 is achieved.

13. The method according to claim 12, wherein said method of formulating further comprises removing any precipitate formed.

14. The method according to claim 13, wherein said precipitate is removed by filtration.

15. The method according to claim 14, wherein said filtration is conducted through a 30 micron filter.

* * * * *

UNITED STATES PATENT AND TRADEMARK OFFICE
CERTIFICATE OF CORRECTION

PATENT NO. : 5,599,933
DATED : February 4, 1997
INVENTOR(S) : Kaiser, Richard

It is certified that error appears in the above-indentified patent and that said Letters Patent is hereby corrected as shown below:

In Column 1, line 19: "often mined by" should read --often ruined by--.

IN THE CLAIMS:
In Claim 5, Column 10, line 7: "claim 1" should read --claim 4--.

Signed and Sealed this

Tenth Day of June, 1997

BRUCE LEHMAN

*Attest:*

*Attesting Officer*　　　　*Commissioner of Patents and Trademarks*